United States Patent

Gale et al.

Patent Number: 4,788,062
Date of Patent: Nov. 29, 1988

[54] TRANSDERMAL ADMINISTRATION OF PROGESTERONE, ESTRADIOL ESTERS, AND MIXTURES THEREOF

[75] Inventors: Robert M. Gale, Los Altos; David J. Enscore, Sunnyvale; Diane E. Nedberge, Los Altos; Melinda Nelson, Sunnyvale; Yu-Ling Cheng, Cupertino; Shari B. Libicki, Palo Alto, all of Calif.

[73] Assignee: ALZA Corporation, Palo Alto, Calif.

[21] Appl. No.: 19,162

[22] Filed: Feb. 26, 1987

[51] Int. Cl.$^4$ .............................................. A61F 13/00
[52] U.S. Cl. .................................... 424/449; 424/448
[58] Field of Search ................ 424/448, 449; 914/946, 914/947

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,710,795 | 1/1973 | Higuchi et al. | 128/260 |
| 3,948,262 | 4/1976 | Zaffaroni | 128/260 |
| 4,144,317 | 3/1979 | Higuchi et al. | 424/21 |
| 4,286,592 | 9/1981 | Chandrasekaran | 128/260 |
| 4,291,014 | 9/1981 | Keith et al. | 424/28 |
| 4,299,826 | 11/1981 | Luedders | 514/947 X |
| 4,314,557 | 2/1982 | Chandrasekaran | 128/260 |
| 4,379,454 | 4/1983 | Campbell et al. | 604/897 |
| 4,438,139 | 3/1981 | Keith et al. | 424/28 |
| 4,466,953 | 8/1984 | Keith et al. | 424/449 |
| 4,470,962 | 9/1984 | Keith et al. | 424/448 |
| 4,568,343 | 2/1986 | Leeper et al. | 424/449 |
| 4,568,343 | 2/1986 | Leeper et al. | 604/896 |
| 4,622,218 | 11/1986 | Boder | 514/176 |
| 4,624,665 | 11/1986 | Nuwayser | 424/448 |
| 4,675,009 | 6/1987 | Hynes et al. | 424/448 |
| 4,687,481 | 8/1987 | Nuwayser | 424/449 |
| 4,938,139 | 3/1981 | Kieth et al. | 424/78 |

FOREIGN PATENT DOCUMENTS 0013606 7/1980 Fed. Rep. of Germany .
0013606 7/1980 United Kingdom .

OTHER PUBLICATIONS

Pfister et al., "Controlled Release of Progesterone, Testosterone, Indomethacin, and Propanol from Silicone Membrane and Matrix Devices".
Chien et al., "Enhancement in Transdermal Controlled Delivery of Therapeutic Agents: (I) Progestational Drug-Progesterone".
Tojo et al., "Skin Permeation of Lipophilic Progestational Drugs: Effect of Increased Hydrophilicity".
Goldzieher et al., "The Percutaneous Absorption of Estradiol-17 Beta and Progesterone".
Valia et al., "Long-Term Permeation Kinetics of Estradiol: (III) Kinetic Analyse of the Simultaneous Skin Permeation and Bioconversion of Estradiol Esters".
Tojo et al., "Long-Term Permeation Kinetics of Estradiol:(IV) A Theoretical Approach to the Simultaneous Skin Permeation and Bioconversion of Estradiol Ester.
Chien et al., "Long-Term Permeation Kinetics of Estradiol:(V) Development and Evaluation of Transdermal Bioactivated Hormone Delivery System".

Primary Examiner—Thurman K. Page
Assistant Examiner—L. R. Horne
Attorney, Agent, or Firm—Edward L. Mandell; Shelley G. Precivale; Steven F. Stone

[57] ABSTRACT

A transdermal delivery system for the administering of progesterone and an estradiol ester alone or in combination utilizing a polymer matrix having the drug(s) along with a permeation enhancer dispersed throughout.

42 Claims, 1 Drawing Sheet

TRANSDERMAL ADMINISTRATION OF PROGESTERONE, ESTRADIOL ESTERS, AND MIXTURES THEREOF

FIELD OF THE INVENTION

This invention relates to systems for drug delivery. More particularly, this invention relates to steroid delivery and still more particularly, but without limitation thereto, this invention relates to the transdermal delivery of progesterone and an estradiol ester, alone or in combination, at therapeutically effective rates.

RELATED PATENT APPLICATIONS

This invention is related to the inventions disclosed in the copending, coassigned patent applications of Cheng, et al for Skin Permeation Enhancer Compositions Using Sucrose Esters, U.S. Ser. No. 07/019,442 of Cheng, et al for Skin Permeation Enhancer Compositions Using Glycerol Monolaurate U.S. Ser. No. 07/019,470 and of Nedberge, et al for Transdermal Contraceptive Formulations, U.S. Ser. No. 07/019,163 filed Feb. 26, 1987.

BACKGROUND OF THE INVENTION

It is well known that the administration of steroids such as estrogens and progestins hormone replacement therapy, aids in the reduction of cyclic hot flashes and other post-menopausal symptoms.

The transdermal route of parenteral delivery of drugs provides many advantages over other administrative routes and transdermal systems for delivering a wide variety of drugs or other beneficial agents are described in U.S. Pat. Nos. 3,598,122; 3,598,123; 4,379,454; 4,286,592; 4,314,557 and 4,568,343, for example, all of which are incorporated herein by reference.

However, despite the development of the art, there has remained a continuing need for improved techniques of providing female users of said medications with basal blood levels of estrogens and progestins.

The present invention delivers therapeutically effective rates of select steroids and offers the advantages of: greatly increased drug bioavailability compared to oral or intramuscularly administered drugs, convenient termination of therapy and improved compliance.

Both estrogen (provided by an estradiol ester) and progesterone are needed to alleviate post-menopausal symptoms: the former to reduce cyclic hot flashes and most other common symptoms and the latter to reduce breakthrough bleeding and minimize endometrial hyperplasia. This invention provides for delivering an estradiol ester and progesterone by means of separate transdermal applications or combined together in a single delivery system.

SUMMARY OF THE INVENTION

An object of the present invention is to provide steroid delivery by means of transdermal systems.

A further object is to deliver progesterone and estradiol esters alone or in combination, at therapeutically effective rates.

A still further object of the present invention is to deliver steroids transdermally using skin permeation enhancers such as fatty acid esters.

An even further object is to provide a method for the transdermal administration of progesterone and an estradiol ester, alone or in combination.

These and other objects have been demonstrated by the present invention wherein a transdermal system is designed using a polymer matrix containing a permeation enhancer and the desired drug(s).

BRIEF DESCRIPTION OF THE DRAWING

The invention will be described in further detail with reference to the accompanying drawings wherein.

DESCRIPTION OF THE PREFERRED EMBODIMENT

This invention utilizes principles of transdermal drug delivery to provide a novel system for effectively administering steroids. Of particular significance is the use of a co-delivered permeation enhancer such as sucrose monococoate or glycerol monoolate, to aid in steroid delivery across the skin.

This invention is directed towards administration of progesterone, an estradiol ester, and combinations thereof. This invention finds particular application in delivering progesterone in combination with an estradiol ester selected from the group consisting of: estradiol-17-acetate, estradiol-3,17-diacetate, estradiol-17-valerate, estradiol-17-heptanoate and estradiol-17-cypionate.

Figure 1:
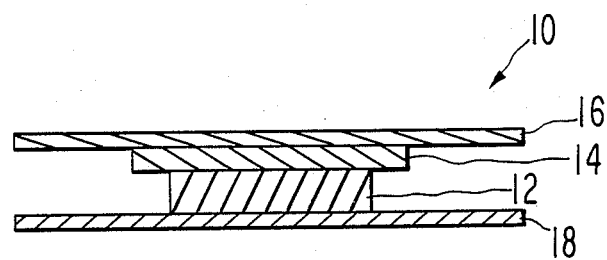
FIG. 1 is a cross-sectional view of one embodiment of the transdermal drug delivery system according to this invention.

One embodiment of the invention is best understood with reference to FIG. 1, which illustrates a transdermal drug delivery system 10. Fabrication of the system 10 begins first with mixing the polymer, permeation enhancer and drugs together to obtain a uniform blend which forms the drug reservoir 12.

This blend is then extruded onto an occlusive backing 14, and calendered to yield a drug reservoir thickness of about 4–15 mils. The backing 14 is made from a material or combination of materials that are substantially impermeable to the components of the reservoir 12.

Means 16 for maintaining the system on the skin may either be fabricated together with or provided separately from the remaining elements of the system which means in the embodiment of FIG. 1 takes the form of an adhesive overlay. The reservoir 12 may also have a small amount of tackifier present to aid means 16 in adhesion of the system 10.

The impermeable backing 14 is preferably sized slightly larger than the reservoir 12 to provide a peripheral area around reservoir 12 which is free of any permeation enhancer. Permeation enhancers suitable for use with steroids, often adversely affect the adhesive properties of pharmaceutically acceptable contact adhesives. The embodiment of FIG. 1 seeks to alleviate this incompatibility by providing an oversized backing 14 to preclude any direct permeation enhancer-adhesive contact.

The drug reservoir 12 is then laminated to a strippable release liner 18 which is at least as large as the largest of the elements of system 10. In the embodiment of FIG. 1, the liner 18 must be as large as the means 16. The liner 18, adapted to be removed prior to application, would normally be included in the packaged product.

Various materials suited for the fabrication of the various layers are disclosed in the aforementioned patents.

The polymer matrix is preferably anhydrous and suitable materials include, without limitation, natural and synthetic rubbers or other polymeric material, thickened mineral oil, or petroleum jelly. The preferred embodiment according to this invention is fabricated from an ethylene/vinylacetate (EVA) copolymer of the type described in U.S. Pat. No. 4,144,317, preferably those having a vinylacetate (VA) content in the range of about 28 to 60 weight percent (w % VA). Particularly good results have been obtained using an EVA copolymer of 40 w % vinylacetate content.

The permeation enhancer can be one of a variety of surfactants or fatty acid esters, including but not limited to the following: sucrose monolaurate (SML), glycerol monooleate (GMO), glycerol monolaurate (GML), polyethylene glycol monolaurate (PEGML), propylene glycol laurate, propylene glycol dipelarginate and neopentyl glycol dicaprate.

The drug is preferably dispersed through the matrix at a concentration in excess of saturation to maintain unit activity. The amount of excess is determined by the intended useful life of the system. The permeation enhancer is initially dispersed through the reservoir at a predetermined activity (fraction of solubility). The optimal permeation enhancer activity must be determined for each individual enhancer. This activity may be anywhere within the range of 0.1 to unit activity. The limits are set by the irritation level and the effects of the enhancer on the polymer matrix or adhesive, as well as its effectiveness as a permeation enhancer.

Figure 2:
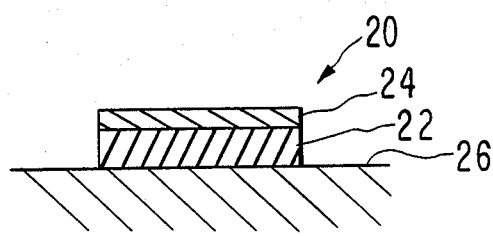
FIG. 2 is a cross-sectional view of another embodiment of the transdermal drug delivery system of this invention.

A second embodiment of the invention is shown in FIG. 2. The transdermal drug delivery system 20 comprises a drug reservoir 22 and an occlusive backing 24. In addition, a strippable release liner (not shown) would preferably be provided on the system prior to use as described with respect to FIG. 1 and removed prior to application to the skin 26.

In this embodiment of the invention, the steroid delivery system is manufactured by combining an adhesive mixture with a skin permeation enhancer and the desired drug or drug combination. This, in essence, creates an adhesive matrix having the drug and permeation enhancer dispersed throughout.

The drug reservoir 22 is made up of a permeation enhancer, the drug(s) and an adhesive mixture. The adhesive, which forms the polymer matrix can be an elastomer/tackifier mix or alternately, a combination of a high and low molecular weight polymer along with an oil. Additionally, the matrix could be self adhering without requiring any tackifier, as is generally the case with acrylate polymers.

The preferred system uses EVA as the elastomer. Typical suitable tackifiers are fully hydrogenated aromatic hydrocarbon resins. Successful results have been achieved with use of the Hercules, Inc. (Wilmington, Del.) product line sold under the trade name Staybelite Ester ™. Specifically, Staybelite Ester #5 has been used.

For the embodiment illustrated in FIG. 2 a suitable composition by weight is: 60–94.5 w % elastomer and tackifier combined (polymer matrix), 5–30 w % permeation enhancer and 0.5–10 w % drug. Though by no means limiting these ranges have proven to be successful as is shown by the following example.

EXAMPLE I

A transdermal therapeutic system as described with respect to FIG. 2 for administration of progesterone was formulated from 10 w % progesterone, 25 w % sucrose monolaurate, 27 w % Staybelite Ester #5 (Hercules, Inc.) tackifier and 38 w % EVA 40 (40 w % VA content). The system was applied to excised human epidermis for 4 days and the progesterone flux measured using a drug flux cell apparatus equilibrated to 37° C. The flux through two epidermis samples averaged 2.0 $\mu g/cm^2$-hr and 3.8 $\mu g/cm^2$-hr, respectively, over a four day period.

The same formulation was tested on a human subject by application of an 80 $cm^2$ patch. Measurement of the progesterone blood level after an 8 hour period indicated an increase in progesterone of 40 ng/dl over baseline.

Figure 3:
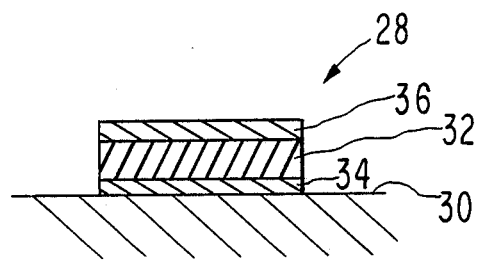
FIG. 3 is a cross-sectional view of still another embodiment of the transdermal drug delivery system according to this invention.

FIG. 3 is an alternate embodiment of the invention, depicting a self-adhering transdermal drug delivery system 28, that is designed to be placed on unbroken skin 30. Similar to FIG. 1, the drug reservoir 32 is comprised of a polymer matrix with the drug(s) and permeation enhancer dispersed throughout. The presence of an in-line contact adhesive layer 34 precludes the need for a tackifier in the reservoir.

The adhesive also has an amount of permeation enhancer present. In this manner, the layer 26 also acts as an in-line release rate-controlling contact adhesive. Specifically, it is the permeation enhancer release rate which is being controlled. Alternately, the adhesive may act to control the drug release rate, or it may have no drug release rate control function at all.

The drug reservoir 32 is extruded onto an occlusive backing 36 and subsequently laminated to the adhesive 34. In addition, a strippable release liner (not shown) would preferably be provided on the system prior to use as described with respect to FIG. 1 and removed prior to application to the skin 30. The system 28 is calendered to a 4–15 mil drug reservoir 32 thickness, followed by lamination to the release liner.

The fabrication process is done on a large scale, with systems for individual usage being die-cut from the laminated web for commercial packaging.

The combination of materials and drugs used in this invention provide for a system ranging in size from 5–80 $cm^2$ and containing sufficient permeation enhancer and drug(s) to maintain steady state blood levels for time periods up to seven days. In vivo delivery rates achievable with this invention are up to 24 mg/day of progesterone and about 25–250 $\mu g$/day of estradiol ester, preferably 50–150 $\mu g$/day.

The embodiments and applications of this invention are best understood in light of the following.

EXAMPLE II

A transdermal therapeutic system as described with respect to FIG. 2, for administration of estradiol valerate was formulated from: 5.0 w % estradiol valerate, 20.0 w % sucrose monolaurate, 34.5 w % Staybelite Ester #5 and 40.5 w % EVA 46 (46 w % VA content). Measurement of the plasma estradiol level after a 24 hour application period on a human volunteer, indicated an increase of 80 pg/ml over baseline.

The following table provides data on the maximum increase in estradiol levels following application (24 hours) of prototype transdermal systems according to this invention, on male subjects. The systems are comprised of 40% or 46% vinylacetate content EVA (EVA 40 or EVA 46); a permeation enhancer selected from the group consisting of GMO, SML, PEGML and GML; Staybelite Ester #5 (tackifier); and ethinyl estradiol (drug).

TABLE I

| Polymer | FORMULATION (weight percent) Enhancer | Tackifier | Drug | ESTRADIOL CONCENTRATION (pg/ml) |
|---|---|---|---|---|
| 40.5% EVA 46 | 20% GMO | 34.5% | 5% | 42 |
| 40.5% EVA 46 | 20% SML | 34.5% | 5% | 46 |
| 40.6% EVA 40 | 25% PEGML | 28.4% | 6% | 16 |
| 36.1% EVA 40 | 25% GML | 28.9% | 10% | 96 |

EXAMPLE III

A monolithic transdermal system can be prepared by melt blending 33 parts EVA (40 w %) with 25 parts GML, 32 parts Staybelite Ester No. 5, 5 parts estradiol valerate and 5 parts progesterone. This mixture would be extruded and calendered to a thickness of 12 mils between an occlusive backing film and a strippable liner film. Individual systems can be rotary die cut with an area of 50 cm². When applied to the skin of human patients, therapeutic blood levels of both medicinal agents will be achieved after a period of about 6 hours.

There are numerous embodiments which provide for the ultimate use of this invention. The systems of this invention can be designed in a variety of ways so as to have an effective life of up to 7 days and to deliver progesterone, an estradiol ester, or mixtures of the two. Preferably a 7 day system would be used. In this manner, four of these 7 day systems packaged together, would provide treatment of post-menopausal symptoms for a one month (28 day) time period.

Estrogen is useful in treating post-menopausal symptoms, while progesterone is useful in countering the side effects associated with estrogen treatment. Therefore, since they serve different purposes, progesterone and an estradiol ester may be delivered together or separately, with the delivery mode varying from system to system.

In one example, an estradiol ester can be delivered alone for the first 14 days and an estradiol ester/progesterone mixture can be delivered for the second 14 days.

In another example, an estradiol ester can be delivered alone for the first 14 days and progesterone can be delivered alone the second 14 days.

In still another example, an estradiol ester is delivered for 7 days, followed by delivery of an estradiol ester/progesterone mixture for 14 days, followed lastly by delivery of progesterone for 7 days.

An even further example is where an estradiol ester/progesterone mixture is delivered for the entire 28 days but the delivery ratio of the two drugs varies within the time period. These examples are illustrative and are not intended to be limiting as there are a variety of regimens contemplated by this invention.

This invention has been described in detail with particular reference to certain preferred embodiments thereof, but it will be understood that variations and modifications can be effected within the spirit and scope of the invention.

What is claimed is:

1. A composition of matter for the transdermal administration of a drug selected from the group consisting of progesterone, an estradiol ester and mixtures thereof, comprising said drug and a skin permeation enhancer selected from the group consisting of sucrose monolaurate, glycerol monooleate, glycerol monolaurate, propylene glycol laurate, and neopentyl glycol dicaprate.

2. The composition of claim 1 wherein said drug is present in an amount in excess of its saturation concentration in said carrier.

3. The composition of claim 1 wherein said permeation enhancer is present at a predetermined concentration such that it has an activity within the range of about 0.1 to unit activity.

4. The composition of claim 1 wherein said drug is progesterone.

5. The composition of claim 1 wherein said drug is an estradiol ester.

6. The composition of claim 1 wherein said drug is a combination of progesterone and an estradiol ester.

7. The composition of claim 1 which further comprises an adhesive.

8. The composition of claim 7 wherein said adhesive is an adhesive mixture forming said matrix, selected from the group consisting of an elastomer and tackifier mix, and a high molecular weight polymer, low molecular weight polymer and oil mix.

9. The composition of claim 7 wherein said adhesive is an in-line contact adhesive.

10. The composition of claim 9 wherein said adhesive is further comprised of a permeation enhancer.

11. The composition of claim 9 wherein said adhesive controls the rate of release of drug from said composition.

12. The composition of claim 9 wherein said adhesive controls the rate of release of permeation enhancer from said composition.

13. A method for the transdermal administration of a drug selected from the group consisting of progesterone, an estradiol ester and mixtures thereof which comprises placing a matrix containing said drug in drug transmitting relationship to the skin in the presence of a permeation enhancer selected from the group consisting of sucrose monolaurate, glycerol monooleate, glycerol monolaurate, propylene glycol laurate, and neopentyl glycol dicaprate.

14. The method of claim 13 wherein said drug is at unit activity.

15. The method of claim 13 wherein said permeation enhancer has an activity within the range of about 0.1 to unit activity.

16. The method of claim 13 wherein said drug is progesterone.

17. The method of claim 16 wherein said progesterone is delivered through the skin at a rate of up to about 24 mg/day.

18. The method of claim 13 wherein said drug is an estradiol ester.

19. The method of claim 18 wherein said estradiol ester is delivered through the skin at a rate of about 25–250 μg/day.

20. The method of claim 18 wherein said estradiol ester is delivered through the skin at a rate of about 50–150 μg/day.

21. The method of claim 13 wherein said drug is a combination of progesterone and an estradiol ester.

22. The method of claim 21 wherein said progesterone is delivered through the skin at a rate of about 24 mg/day and said estradiol ester is delivered through the skin at a rate of about 25–250 μg/day.

23. The method of claim 21 wherein said progesterone is delivered through the skin at a rate of about 24 mg/day and said estradiol ester is delivered through the skin at a rate of about 50–150 μg/day.

24. A medical device for the transdermal delivery of a drug for a predetermined time period selected from the group consisting of progesterone, an estradiol ester and mixtures thereof comprising in combination:
  (a) a reservoir means containing said drug and a permeation enhancer selected from the group consisting of sucrose monolaurate, glycerol monooleate, glycerol monolaurate, propylene glycol laurate, propylene glycol dipelarginate and neopentyl glycol dicaprate;
  (b) a means for maintaining said reservoir means in drug and permeation enhancer transmitting relationship to the skin at therapeutically effective rates;
  (c) said drug being present in said reservoir means in amounts sufficient to deliver said drug at said therapeutically effective rates for said predetermined time period; and
  (d) said permeation enhancer being present in said reservoir means in amounts sufficient to deliver said permeation enhancer at said therapeutically effective rates for said predetermined time period.

25. The medical device of claim 24 wherein said means for maintaining said reservoir in drug and permeation enhancer transmitting relationship to the skin is an adhesive overlay.

26. The medical device of claim 24 wherein said means for maintaining said reservoir in drug and permeation enhancer transmitting relationship to the skin is an in-line contact adhesive.

27. The medical device of claim 24 wherein said drug is progesterone.

28. The medical device of claim 24 wherein said drug is an estradiol ester.

29. The medical device of claim 24 wherein said drug is a combination of progesterone and an estradiol ester.

30. A method for the treatment of post-menopausal symptoms in the human female which comprises transdermally administering progesterone and an estradiol ester at therapeutically effective rates nd durations, said rates and durations defining a 28 day therapeutic regimen, and repeating said regimen at the expiration of the preceding 28 day regimen for so long as therapy is desired.

31. The method of claim 30 wherein said 28 day regimen comprises delivering an estradiol ester for 14 days, followed by delivering a mixture of an estradiol ester and progesterone for 14 days.

32. The method of claim 30 wherein said 28 day regimen comprises delivering an estradiol ester for 14 days, followed by delivering progesterone for 14 days.

33. The method of claim 30 wherein said 28 day regimen comprises delivering an estradiol ester for 7 days, followed by delivering a mixture of an estradiol ester and progesterone for 14 days, followed by delivering progesterone for 7 days.

34. The method of claim 30 wherein said 28 day regimen comprises delivering a mixture of an estradiol ester and progesterone for 28 days.

35. The method of claim 34 wherein the delivery ratio of said estradiol ester to said progesterone varies within the 28 day delivery period.

36. The composition of claim 1 wherein said drug and skin permeation enhancer are dispersed within a carrier.

37. A 28 day transdermal dosage package for the treatment of post-menopausal symptoms comprising in combination, a container containing a plurality of transdermal systems for delivering progesterone and an estradiol ester at therapeutically effective rates and durations, said rates and durations defining a 28 day therapeutic regimen.

38. The package of claim 37 wherein a portion of said systems deliver said estradiol ester and the remainder of said systems deliver a mixture of said estradiol ester and progesterone, wherein said systems delivering the estradiol ester deliver said estradiol ester for the initial 14 day and systems delivering the estradiol ester and progesterone mixture deliver said mixture for the remaining 14 days.

39. The package of claim 37 wherein a portion of said systems deliver said estradiol ester and the remainder of said systems deliver progesterone, wherein said systems delivering the estradiol ester deliver said estradiol ester for the initial 14 days and systems delivering progesterone deliver said progesterone for the remaining 14 days.

40. The package of claim 37 wherein a first portion of said systems deliver said estradiol ester, a second portion of said systems deliver a mixture of said estradiol ester and progesterone and the remainder of said systems deliver progesterone, wherein said systems delivering the estradiol ester deliver said estradiol ester for the initial 7 days, systems delivering a mixture of the estradiol ester and progesterone deliver said mixture for the subsequent 14 days and systems delivering progesterone deliver said progesterone for the remaining 7 days.

41. The package of claim 37 wherein said systems deliver a mixture of said estradiol ester and progesterone.

42. The package of claim 41 wherein said systems have varying amounts of said estradiol ester and progesterone.

* * * * *